United States Patent
Weber (10) Patent No.: US 7,582,115 B2
(45) Date of Patent: Sep. 1, 2009

(54) INTERVERTEBRAL PROSTHESIS

(76) Inventor: Helmut Weber, Engener Strasse 11, 78576 Emmingen-Liptingen (DE)

( * ) Notice: Subject to any disclaimer, the term of this patent is extended or adjusted under 35 U.S.C. 154(b) by 0 days.

(21) Appl. No.: 10/955,103

(22) Filed: Sep. 30, 2004

(65) Prior Publication Data
US 2006/0069437 A1    Mar. 30, 2006

(51) Int. Cl.
*A61F 2/44* (2006.01)
(52) U.S. Cl. .................................. 623/17.14
(58) Field of Classification Search .... 623/17.11–17.16
See application file for complete search history.

(56) References Cited

U.S. PATENT DOCUMENTS

| | | | | |
|---|---|---|---|---|
| 2,761 | A * | 8/1842 | Banks | 295/31.1 |
| 4,207,627 | A * | 6/1980 | Cloutier | 623/20.21 |
| 4,759,766 | A | 7/1988 | Buettner-Janz et al. | |
| 5,401,269 | A * | 3/1995 | Buttner-Janz et al. | 623/17.15 |
| 6,368,350 | B1 * | 4/2002 | Erickson et al. | 623/17.14 |
| 6,770,095 | B2 * | 8/2004 | Grinberg et al. | 623/17.14 |
| 6,927,504 | B2 | 8/2005 | Olijnyk et al. | |
| 6,936,071 | B1 * | 8/2005 | Marnay et al. | 623/17.15 |
| 2004/0002761 | A1 | 1/2004 | Rogers et al. | |
| 2004/0153157 | A1 | 8/2004 | Keller | |
| 2004/0243240 | A1 * | 12/2004 | Beaurain et al. | 623/17.14 |
| 2005/0021145 | A1 * | 1/2005 | de Villiers et al. | 623/17.14 |
| 2006/0190082 | A1 * | 8/2006 | Keller et al. | 623/17.11 |

FOREIGN PATENT DOCUMENTS

| | | |
|---|---|---|
| DE | 20315611 U1 | 1/2004 |
| DE | 202004009542 U1 | 9/2004 |
| DE | 202004009542 U1 * | 9/2004 |

* cited by examiner

*Primary Examiner*—Thomas C Barrett
*Assistant Examiner*—James L Swiger
(74) *Attorney, Agent, or Firm*—Akerman Senterfitt; Peter A. Chiabotti (57) ABSTRACT

The invention concerns an intervertebral prosthesis comprised of a first prosthetic end plate (20) and a second prosthetic end plate (30) as wall as a prosthetic core (10) located between the first prosthetic end plate (20) and the second prosthetic end plate (30), wherein the first prosthetic end plate (20) has a hemispherical shaped recess (21) with a radius (R3), in which a hemispherical segment (11) of the prosthetic core (10) engages, and wherein the second prosthetic end plate (30) has an essentially planar recess (31), in which an essentially flat segment (15) of the prosthetic core (10), connected to the hemispherical segment (11), engages, wherein the essentially flat segment (15) of the prosthetic core (10) is slideably moveable in the essentially planar recess (31).

15 Claims, 5 Drawing Sheets

INTERVERTEBRAL PROSTHESIS

BACKGROUND OF THE INVENTION

1. Field of the Invention

The invention concerns an intervertebral prosthesis according to the precharacterizing portion of Patent Claim 1.

2. Description of the Related Art

Three-part intervertebral prosthesis are known, for example from EP 0 176 728 A1 or WO 02/08018 A1, comprised of two prosthetic end plates or cover plates, between which a prosthetic core is provided. The prosthetic end plates are comprised of a circular shaped or elliptical shaped disk, which exhibits a hemispherical recess on one side. The prosthetic core is in the shape of a circular disk, exhibiting on both sides respectively an axially disposed hemispherical segment and, running around the outer edge, an axially projecting ring segment. In the assembled condition of the intervertebral prosthesis the hemispherical segments of the prosthetic core lie in the hemispherical recesses of the two prosthetic end plates.

If the intervertebral prosthesis is introduced into the intervertebral space as replacement for a defective disk, which had been removed during an operation, then the two prosthetic end plates are respectively attached to respectively one vertebra and the prosthetic core is introduced between the prosthetic end plates. The cooperation of the hemispherical segments with the hemispherical shaped recesses makes possible a rotational movement of the two adjacent vertebrae.

Also known from, for example, WO 02/080818 A1 are three-part intervertebral prosthesis with a prosthetic core, which exhibits only one hemispherical segment and in place of the second hemispherical segment exhibits a flat segment. This flat segment is fixed into a correspondingly shaped recess in the one prosthetic end plate, since the movement of the one hemispherical segment in the hemispherical shaped recess is sufficient for a tilt and rotation movement of both prosthetic end plates relative to each other.

The described intervertebral prosthesis makes possible a rotation movement of the two vertebral bodies connected to each other via the prosthetic end plates about a point of rotation, which lies in the axis of the rotation-symmetric prosthetic core. During rotation and movement of an upper body with a healthy vertebral column however the rotation point does not, as a rule, lie in the center of the vertebral disk, but rather outside of the intervertebral space. The intervertebral prosthesis according to the state of the art thus exhibits a defect, of not optimally simulating the natural movement of the vertebral column.

SUMMARY OF THE INVENTION

The task of the invention is thus comprised therein, of providing an intervertebral prosthesis, which exhibits an improved simulation behavior of the natural movement of the spinal column.

The invention is solved by an intervertebral prosthesis with the characterizing features of Patent Claim 1.

Advantageous embodiments and further developments of the invention are set forth in the dependent claims.

In accordance with the invention the intervertebral prosthesis includes a prosthetic core, which includes a hemispherical segment and a flat segment, wherein the flat segment of the prosthesis core engages in a substantially planar recess of one of the two prosthetic end plates, wherein in accordance with the invention the flat segment of the prosthetic core is slideably moveable in the planar recess. As a result of the design of this type of intervertebral prosthesis there is made possible, in addition to the possible tilt movement of the two prosthetic end plates relative to each other, a relative movement of the two prosthetic end plates in a plane parallel to the plane of the prosthetic end plates relative to each other. In a movement of the vertebral column the pivot or rotation point of the movement thus does not necessarily lie on the axis of the prosthetic core. By the combination tilt and translation movement a pivot point can be simulated outside the intervertebral region.

In an advantageous further development of the invention the essentially planar recess exhibits a substantially round cross-section. This type of recess is particularly simple to produce from a manufacturing prospective.

Preferably, the flat segment of the prosthetic core exhibits a substantially round cross-section. A design of the prosthetic core of this type is likewise particularly simple to produce. In particular, the cooperation of a substantially round recess and a substantially round flat segment of the prosthetic core enables an optimal movement of the prosthetic core relative to the prosthetic end plate, since no amount of canting of the prosthetic core in the planar recess of the prosthetic end plate can occur and the prosthetic core can freely turn.

Preferably the diameter of the flat segment of the core is smaller than the diameter of the essentially planar recess of the end plate. In this manner the movement of the flat segment of the prosthetic core in the essentially planar recess is made possible.

In an advantageous further development of the invention the base of the essentially planar recess exhibits a curvature. A curvature of this type makes possible, in addition to the translation movement of the prosthetic core in the essentially planar recess of the prosthetic end plate, a slight tilt movement, which further improves the simulation behavior of the intervertebral prosthesis.

Preferably the radius of the curvature of the essentially planar recess is five to ten times as large as the radius of the hemispherical recess. The base of the essentially planar recess therewith continues to be essentially planar and enables only very slight tilt movement, while the major part of the tilt movement is brought about by the cooperation of the hemispheric segment of the prosthetic core in the hemispherical recess of the prosthetic end plate.

Preferably the base of the flat segment is curved. In particular, in the case of a matching or coordination of the curvature of the flat segment to the curvature of the base of the planar recess, a translation movement of the prosthetic core in the essentially planar recess is made possible, which on the one hand makes possible a slight tilt movement, while however continuously maintaining contact between the prosthetic core and the broad bottom surface of the essentially flat segment on the base surface of the essentially planar recess.

Preferably the flat segment of the prosthetic core, beginning from the upper surface of the hemispherical segment, widens conically outwardly. By a design of this type of the flat segment of the prosthetic core, a reaching behind of the projections formed on the prosthetic end plate is made possible, so that a popping out of the prosthetic core out of the intermediate space between the two prosthetic end plates can reliably be prevented.

Preferably the essentially planar recess narrows conically inwards beginning from the base surface. Thereby a circumferential protrusion is formed, which engages a correspondingly shaped circumferential groove of the prosthetic core and prevents a popping out or pressing out of the prosthetic core out of the intermediate space between the two prosthetic end plates reliably.

Preferably the angle between the outer surface of the flat segment and the base surface of the flat segment of the prosthetic core corresponds to the angle of the outer surface of the essentially planar recess relative to the base surface of the essentially planar recess of the prosthetic end plate. In this manner, a guidance of the prosthetic core in the recess of the prosthetic end plate is made possible in the manner of a dovetail joint. The prosthetic core is therewith particularly reliably maintained in the intermediate space in the essentially planar recess of the prosthetic end plate and, therewith, between the two prosthetic end plates.

Preferably the surfaces of the two prosthetic end plates, beginning from the outer edge of the hemispherical shaped recess or, as the case may be, the essentially planar recess, are formed with an incline which decreases going outwards. Thus, in the case of a tilting of the two prosthetic end plates relative to each other, it can be achieved therewith, in the case of appropriate design of the inclination, that in the case of a maximal tilting of the two prosthetic end plates relative to each other the outer regions of the two prosthetic end plates contact along a flat line instead of a contact point on the inward facing surface, whereby the load is better distributed and damage of the prosthetic end plates can be avoided.

BRIEF DESCRIPTION OF THE DRAWINGS

An embodiment of the invention will now be described in greater detail on the basis of the following FIGURES.

There is shown:

FIG. 1 a side view of a prosthetic core of an intervertebral prosthesis according to the invention, FIG. 2a a top view on the inward facing surface of the second prosthetic end plate of an intervertebral prosthesis according to the invention, FIG. 2b a top view on the outward facing surface of the prosthetic end plate of FIG. 2a, FIG. 3a a side view of an embodiment of an intervertebral prosthesis according to the invention, FIG. 3b a further side view of the intervertebral prosthesis of FIG. 3a, FIG. 4a an axial section along the minor axes of the two prosthetic end plates through the inventive intervertebral prosthesis with prosthetic end plates tilted relative to each other, FIG. 4b an axial section along the main axes of the two prosthetic end plates through the inventive intervertebral prosthesis of FIG. 4a with prosthetic end plates tilted relative to each other, FIG. 5a an axial section along the minor axes of the two prosthetic end plates through the inventive intervertebral prosthesis with prosthetic end plates tilted relative to each other in a further position, FIG. 5b an axial section along the main axes of the two prosthetic end plates through the inventive intervertebral prosthesis of FIG. 5a with prosthetic end plates tilted relative to each other in a further position, FIG. 6a an axial section along the minor axes of the two prosthetic end plates through the inventive intervertebral prosthesis with prosthetic end plates oriented parallel to each other, FIG. 6b an axial section along the main axes of the two prosthetic end plates through the inventive intervertebral prosthesis of FIG. 6a with prosthetic end plates oriented parallel to each other, FIG. 7a an axial section along the minor axes of the two prosthetic end plates through the inventive intervertebral prosthesis with prosthetic end plates tilted relative to each other in a further position, FIG. 7b an axial section along the main axes of the two prosthetic end plates through the inventive intervertebral prosthesis of FIG. 7a with prosthetic end plates tilted relative to each other in a further position, FIG. 8a an axial section along the minor axes of the two prosthetic end plates through the inventive intervertebral prosthesis with prosthetic end plates tilted relative to each other in a further position, FIG. 8b an axial section along the main axes of the two prosthetic end plates through the inventive intervertebral prosthesis of FIG. 8a with prosthetic end plates tilted relative to each other in a further position, FIG. 9 enlarged representation of the axial section according to FIG. 8a and FIG. 10 a schematic top view of a vertebra with attached prosthetic end plate.

DETAILED DESCRIPTION OF THE INVENTION

Figure 1:
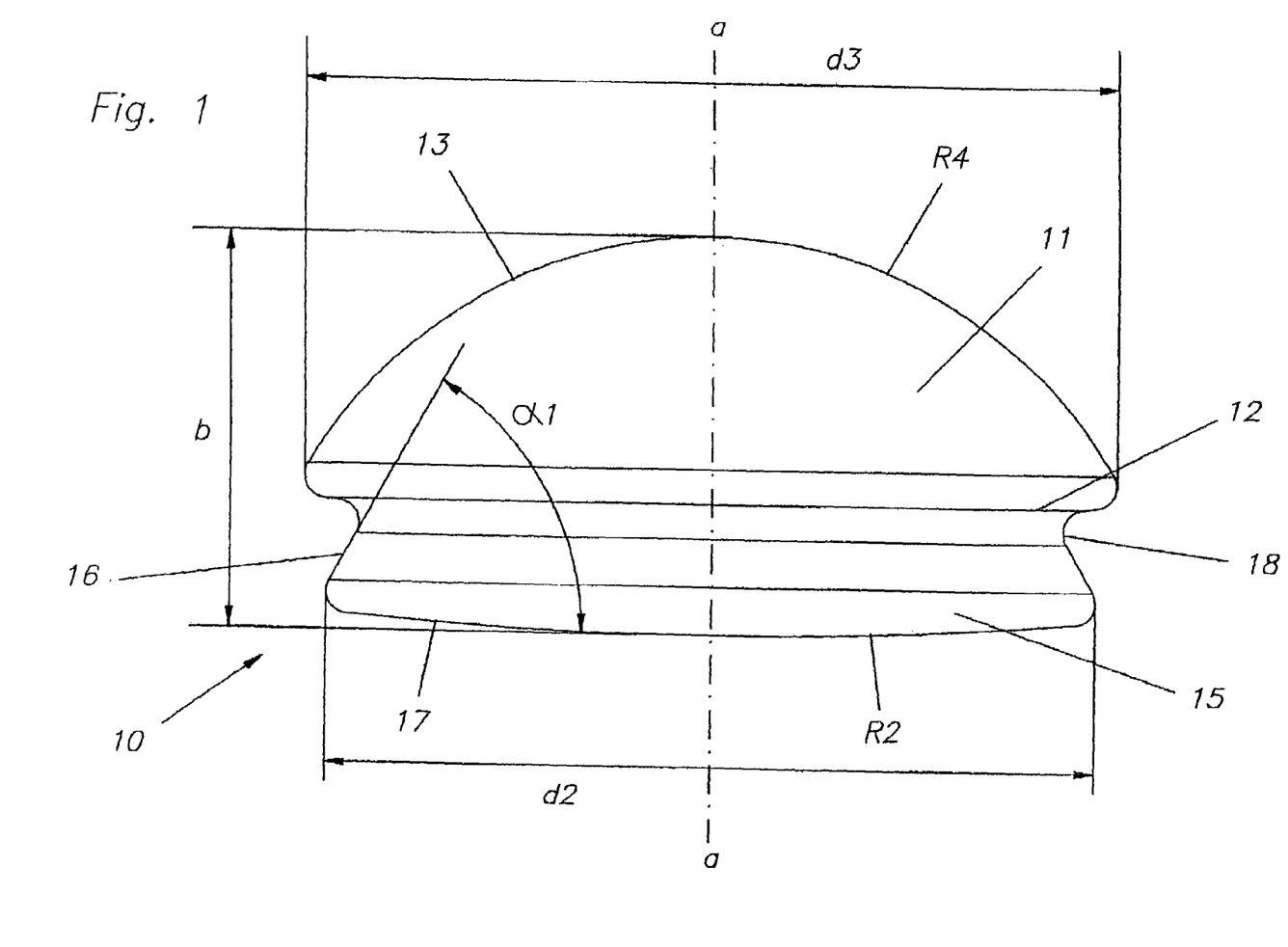

FIG. 1 shows a side view of a prosthetic core 10 according to the invention. The prosthetic core 10 has a hemispherical segment 11 with a curved surface 13 and a planar surface 12. The hemispherical surface 11 is defined by a radius R4. The planar surface 12 of the hemispherical segment 11 has a diameter d3, which corresponds to the greatest radial circumference or dimension of the prosthetic core 10.

Connected to the planar surface 12 of the hemispherical segment 11 is a substantially flat segment 15. The flat segment 15 has an essentially circular cross-section with a diameter d2. The result is a rotational-symmetric prosthetic core 10. The rotation axis of the prosthetic core 10 is shown in FIG. 1.

The flat segment 15 can have a rectangular or square cross-section, wherein however such a design of the prosthetic core 10 provides less than optimal simulation results of the intervertebral prosthesis, since such a prosthetic core 10 cannot freely rotate.

The essentially flat segment 15 exhibits, beginning from the planar surface 12 of the hemispherical segment 11, an outer surface 16 and, running approximately parallel to the planar surface 12, a base surface 17. The outer surface 16 runs at an angle α1 relative to the base surface 17, which is smaller than 90°. Thereby there is produced an essentially flat segment 15, which widens conically outwards beginning from the planar surface 12 of the hemispherical segment 11, that is, widens going towards the base surface 17.

The base surface 17 of the flat segment 15 is curved slightly convex. The curvature of the base surface 17 is characterized by a radius R2. The radius R4 of the hemispherical segment 11 is comparatively substantially smaller, in particular five to ten times smaller, than the radius R2 characterizing the curvature of the base surface 17 of the flat segment 15.

In the illustrated embodiment the radius R4 of the hemispherical segment 11 is approximately 11 mm. The radius R2 characterizing the base surface 17 is 100 mm. The diameter d3 of the planar surface 12 of the hemispherical segment 11 is approximately 19 mm and defines or establishes the greatest radial diameter of the prosthetic core 10. The diameter d2 of the flat segment 15 is in principle smaller than the diameter d3 of the planar surface 12 and in the present case is approximately 18 mm. The prosthetic core 10 has a height b, which in the present case is approximately 9 mm.

In order to select the most suitable intervertebral prosthesis for each intervertebral space, it would be possible of course to utilize larger or smaller prosthetic cores 10, in which the above-mentioned dimensions are adapted to be correspondingly proportional. The diameter d2 of the essentially flat segment 15 is thus in general in the range of between 14 mm and 22 mm. The radius R4 of the hemispherical segment 11 lies between 8 mm and 14 mm, the radius R2 of the curve of the base surface 17 between 80 mm and 120 mm. The other dimensions can be found correspondingly.

The angle α1 between the outer surface 16 and the base surface 17 of the flat segment 15 is in general smaller than 90° and lies preferably between 50° and 80°. In the illustrated embodiment the angle α1 is approximately 70°. By a tilting of the outer surface 16 of the flat segment 15 in this manner a circumferential groove 18 is formed in the transition area between the hemispherical segment 11 and the flat segment 15, in which a correspondingly shaped projection of a prosthetic end plate can engage, in order to securely retain the prosthetic core 10 in the prosthetic end plate.

Figure 2A:
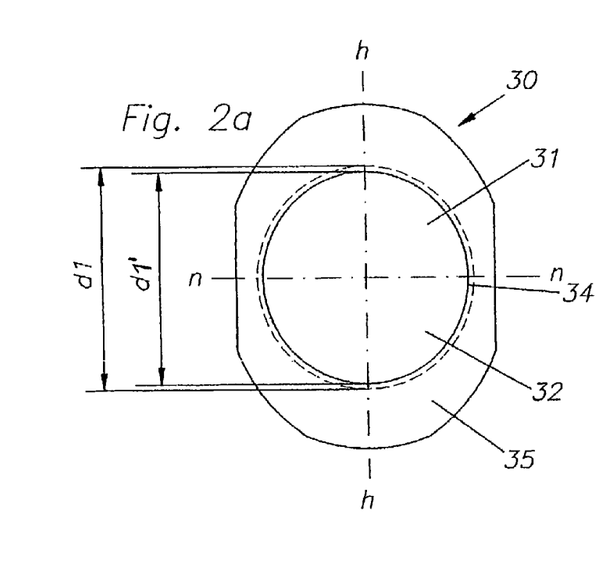
Figure 2B:
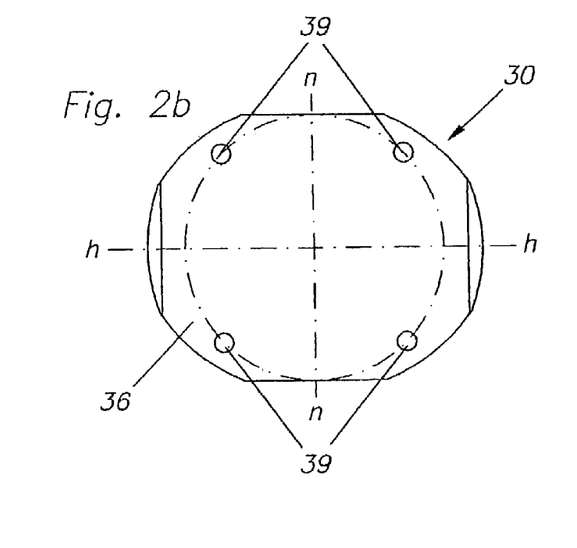

The FIGS. 2a and 2b show a top view from inside and from outside on a second prosthetic end plate 30, which is comprised of an essentially elliptically shaped disk with a main axis h and a minor axis n. The minor apex of the elliptically shaped disk is flattened. The second prosthetic end plate 30 has an inward facing surface 35 and an outward facing surface 36. The inward facing surface 35 includes an essentially planar recess 31, which has an essentially round cross-section with a diameter d1.

Figure 9:
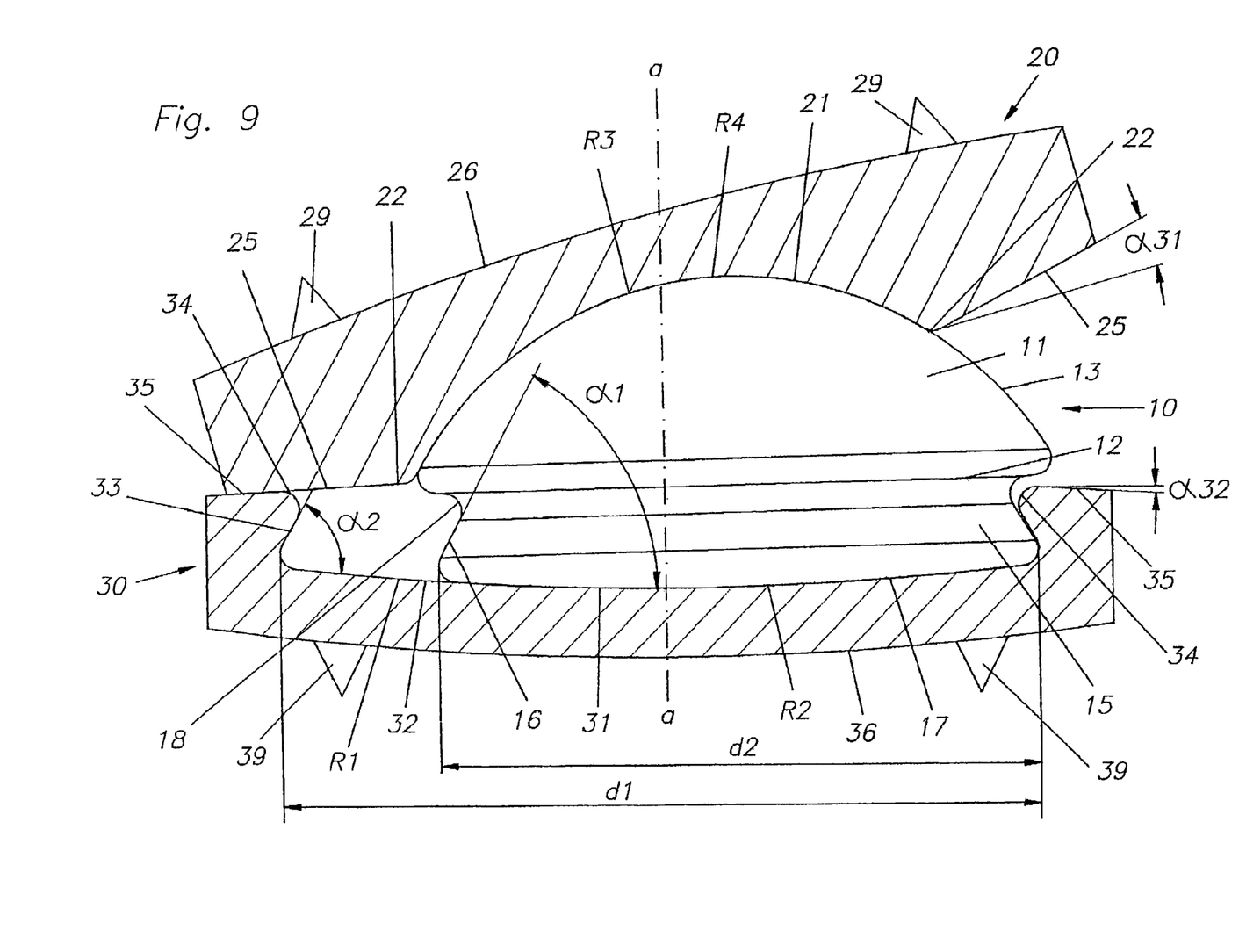

The essentially planar recess 31 is defined by a base surface 32 and an outer wall 33 (see also FIG. 9). The contact line of the inward facing surface 35 of the second prosthetic end plate 30 with the outer wall 33 of the planar recess 31 forms an outer border or lip or rim 34. The outer wall 33 forms, together with the base surface 32 of the essentially planar recess 31, an angle α2 (see FIG. 9), which is small than 902. Thereby the diameter d1 of the base surface 32 of the planar recess 31 is greater than the diameter d1' of the outer edge 34, so that the essentially planar recess 31, beginning from the base surface 32, narrows conically towards inwards. The diameter d1 of the planar recess 31 is approximately 23 mm and can in the case of a larger or smaller intervertebral prosthesis lie between 19 mm and 27 mm.

The base surface 32 of the essentially planar recess 31 has a concave curvature, which is characterized or defined by a radius R1 (see also FIG. 9). The radius R1 of the curvature of the base surface 32 of the essentially planar recess 31 lies between 80 mm and 120 mm and corresponds in the present case to approximately 100 mm.

On the outward facing surface 36 of the second prosthetic end plate 30 there are provided multiple teeth 39, four in the present case, via which the second prosthetic end plate 30 can be affixed to a vertebra.

The recess of the second prosthetic end plate 30 along main axis h corresponds in the illustrated embodiment to 35 mm, the recess along the minor axes n corresponds to 27 mm. It applies as well for the second prosthetic end plate 30 that, in the case of larger or smaller intervertebral prosthesis, the size of the prosthetic end plate 30 can be appropriately, preferably proportionally, adapted.

Figure 3A:
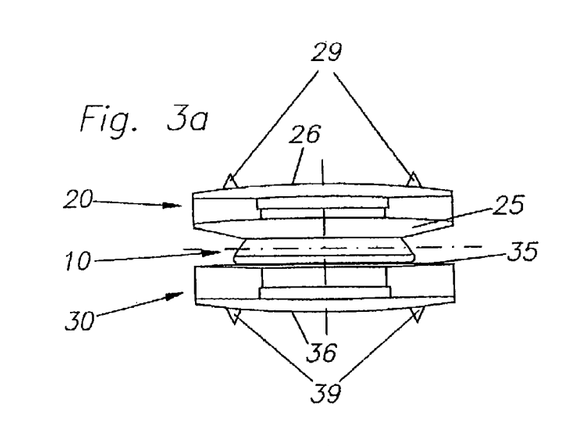
Figure 3B:
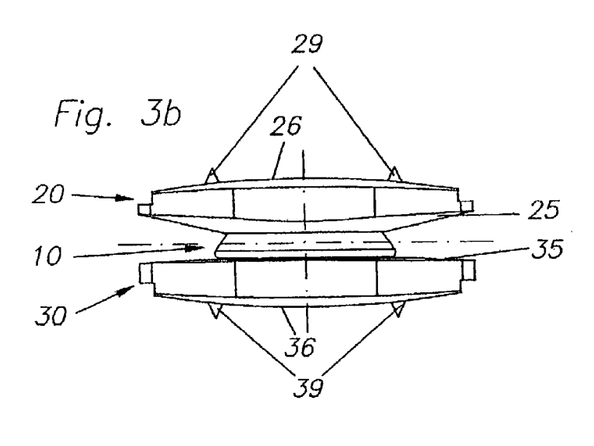

FIGS. 3a and 3b show two side views, respectively, with the direction of view along main axis h or, as the case may be, minor axis n of an intervertebral prosthesis comprised of a first prosthetic end plate 20, an already described prosthetic core 10 and the already described second prosthetic end plate 30. In addition, FIG. 9 shows an axial section through an intervertebral prosthesis in the assembled condition comprised of a prosthetic end plate 20, a prosthetic core 10 and prosthetic end plate 30.

The first prosthetic end plate 20 has an inward facing surface 25 and an outward facing surface 26. On the inward facing surface 25 of the first prosthetic end plate 20 is a hemispherical shaped recess 21, which is defined by a radius R3. The radius R3 in the illustrated embodiment is 11 mm. The contact line between the hemispherical shaped recess 21 and the inward facing surface 25 of the first prosthetic end plate 20 forms an outer edge or border 22. On the outward facing surface 26 of the first prosthetic end plate 20 there are provided multiple teeth 29, via which the first prosthetic end plate can be anchored in the vertebral body. The outer dimensions of the first prosthetic end plate 20 correspond to those of the second prosthetic end plate 30.

In the assembled condition of the intervertebral prosthesis (see FIGS. 4 through 9) the hemispherical segment 11 of the prosthetic core 10 engages in the hemispherical recess 21 of the first prosthetic end plate 20. In order to ensure a good seating of the prosthetic core 10 in the first prosthetic end plate 20, the radius R4 of the hemispherical segment 11 is dimensioned to correspond to the radius R3 of the hemispherical shaped recess 21.

The prosthetic core 10 engages with the flat segment 15 in the essentially planar recess 31 of the second prosthetic end plate 30. In order to make possible a sliding movement of the prosthetic core 10 in the second prosthetic end plate 30, the diameter d1 of the essentially planar recess 31 is larger than the diameter d2 of the flat segment 15 (see in particular FIG. 9).

Further, the curvature of the base surface 17 of the essentially flat segment 15 is dimensioned to correspond to the curvature of the base surface 32 of the essentially planar recess 31. For this, the radius R2 of the flat segment 15 is identical to the radius R1 of the base surface 32 of the planar recess 31. A matching of the curvature in this manner ensures that the prosthetic core 10 lies with the entire base surface 17 on the base surface 32 of the essential planar recess.

Figure 10:
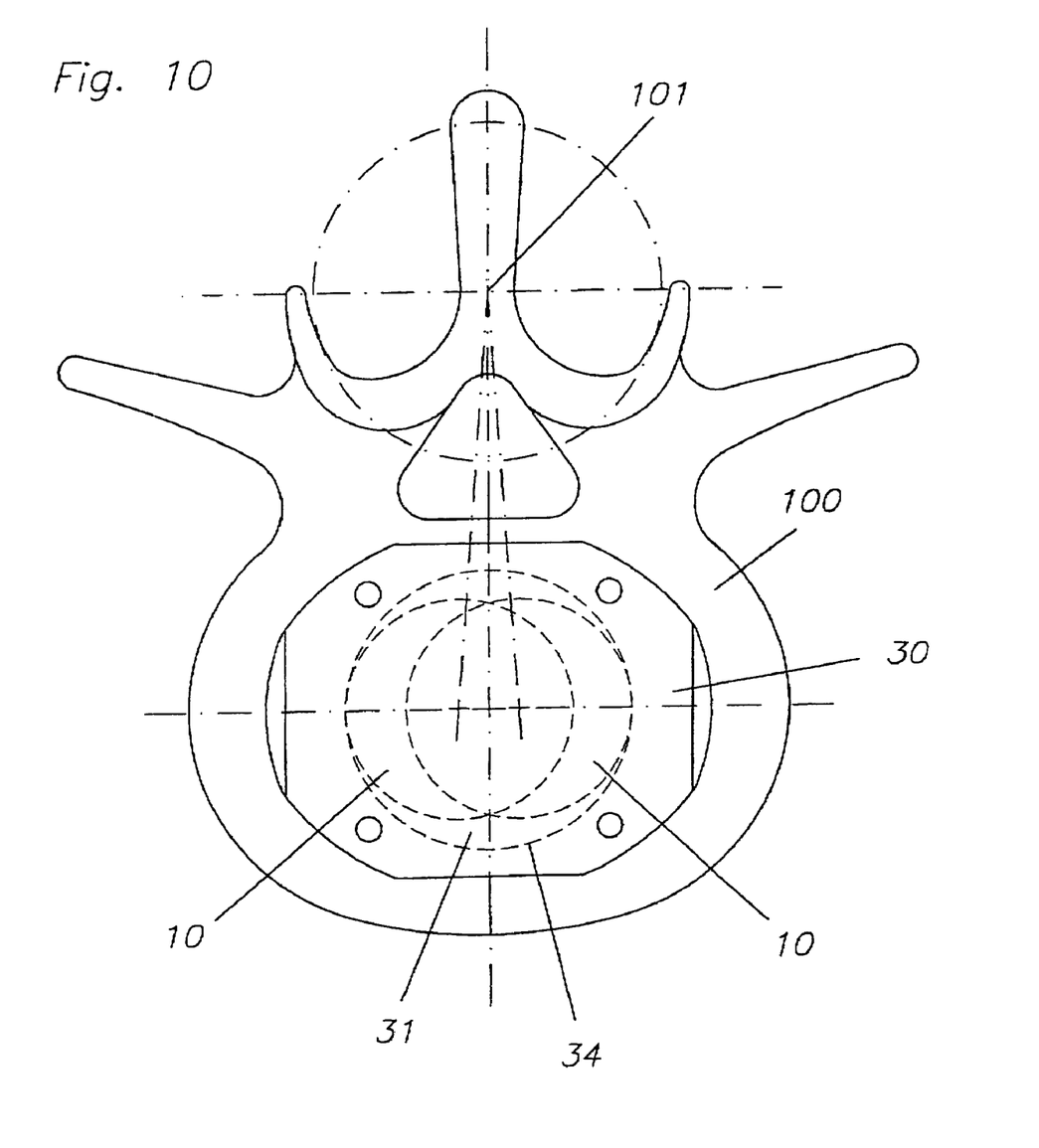

In a relative movement of two adjacent vertebra, to which respectively a first prosthetic end plate 20 or, as the case may be, the second prosthetic end plate 30 are secured via the teeth 29 or, as the case may be, 39, the following is made possible by the inventive intervertebral prosthesis. The tilting movement of the two prosthetic end plates 20 and 30 in any desired direction is made possible by the movement of the hemispherical segment 11 in the hemispherical recess 21. In addition, the prosthetic core 10 is moveable slideably in the essentially planar recess 31. FIG. 10 shows a schematic top view on a vertebra 100, upon which the second prosthetic end plate 30 is secured. FIG. 10 shows how, by the displacement of the prosthetic core 10 in the essentially planar recess 31 of the prosthetic end plate 30 a sliding displacement of the tilt or rotation point 101 makes possible the relative movement of the vertebra in a space outside in the vertebral body 100. A mounting or bearing of the pivot point 101 in this manner provides a better approximation of the actual position or condition of the rotation point of a rotation movement of the upper body, and thus a relative movement between two adjacent vertebra, substantially better than the simulation of the rotation or pivot point on the rotation axis a of the prosthetic core 10 with conventional intervertebral prosthesis. In FIG. 10 two different positions of the prosthetic core 10 in the essentially planar recess 31 of the second prosthetic end plate 30 is schematically shown.

Various relative positions of the first prosthetic end plate 20, the second prosthetic end plate 30 and the prosthetic core 10 are shown in FIGS. 4 through 8. Therein the FIGS. 4a, 5a, 6a, 7a and 8a show respectively a cross-section along the minor axis n through the intervertebral prosthesis, while FIGS. 4b, 5b, 6b, 7b and 8b show a cross-section along the main axis h through the intervertebral prosthesis. For reasons of better overview, in FIGS. 4 through 8 only the first prosthetic end plate 20, the second prosthetic end plate 30 and the prosthetic core 10 are shown with reference numbers. The remaining reference numbers can be found in FIG. 9, which represents an enlarged representation of FIG. 8a, and can be applied analogously to any of FIGS. 4 through 8.

Figure 4A:
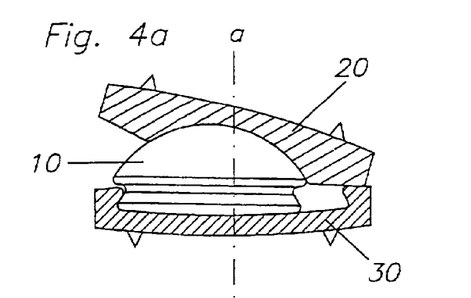
Figure 4B:
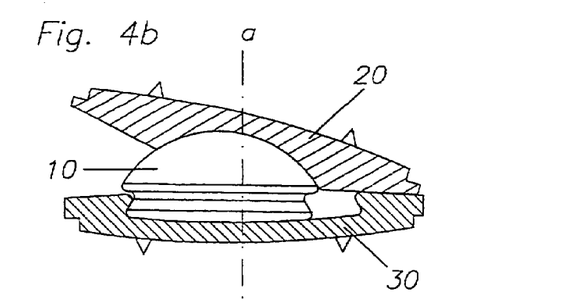
Figure 5A:
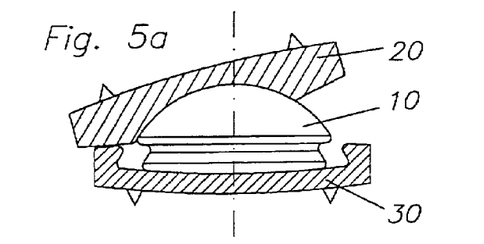
Figure 5B:
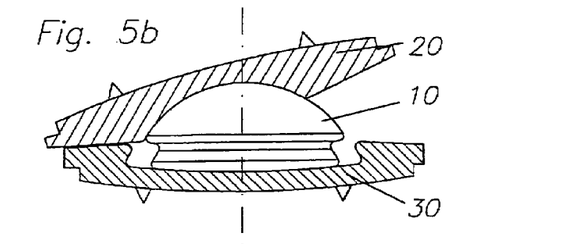
Figure 6A:
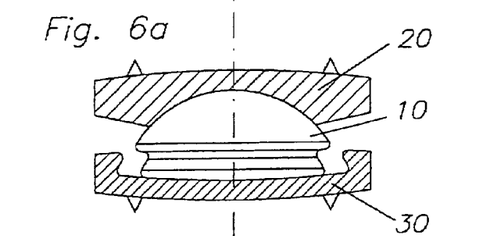
Figure 6B:
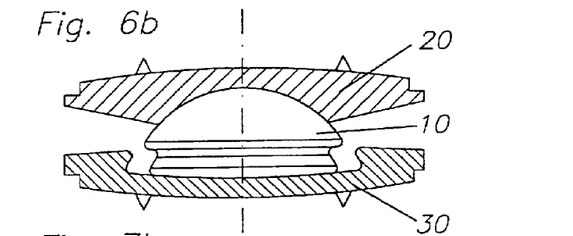
Figure 7A:
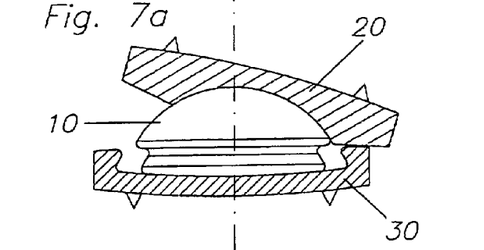
Figure 7B:
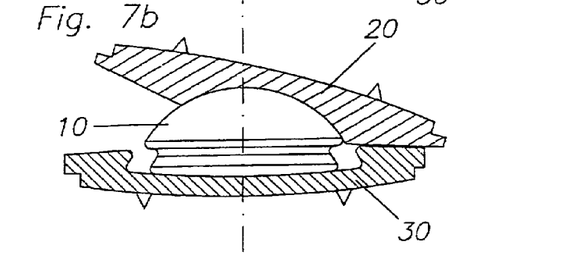
Figure 8A:
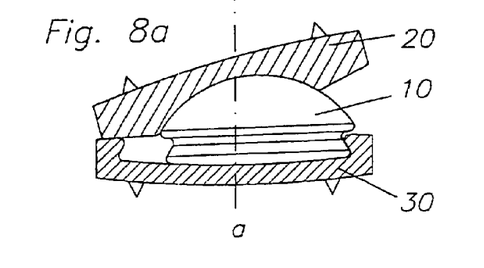
Figure 8B:
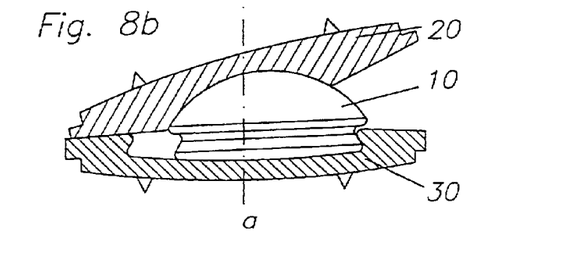

FIGS. 6a and 6b show the intervertebral prosthesis with parallel to each other oriented prosthetic end plates 20 and 30 and the prosthetic core 10 oriented centrally between the first prosthetic end plate 20 and the second prosthetic end plate 30. If, for example, a load is exercised on the ends of the first prosthetic end plate 20 and second prosthetic end plate 30 at the ends lying to the right of the rotation axis in FIGS. 6a and 6b, the first prosthetic end plate 20 tilts, whereby the hemispherical segment 11 slides in the hemispherical recess 12 of the first prosthetic end plate 20. A maximal tilting is shown for example in FIGS. 7a and 7b. The prosthetic core 10 therein remains initially in the centered position. In the case of further loading, the prosthetic core 10 is pressed beginning from the rotation axes towards the left, as shown in FIGS. 4a and 4b. The corresponding relative positions in the case of a loading of the first prosthetic end plate 20 and the second prosthetic end plate 30 on the side to the left of the rotation axes of the prosthetic end plates is shown in FIGS. 5a and 5b or as the case may be 8a and 8b.

As particularly clearly shown in FIG. 9, upon displacement of the prosthetic core 10 within the essentially planar recess 31, the prosthetic core 10 engages against the outer wall 33 of the outer edge 34 in the circumscribing groove 18 of the prosthetic core 10. As a result of the angle α2 diagonal to the base surface 32 running outer wall 33 and the outer surface 16 of the flat segment 15 running at an angle α1 to the base surface 17 of the flat segment 15, a guidance of the prosthetic core 10 in the planar recess 31 is made possible in the manner of a dovetail guidance. For this it is particularly preferred that the angles α1 and α2 are essentially identical. Thereby the prosthetic core 10 is reliably held in the essentially planar recess 31 and cannot be pushed out or pop out of the intermediate space between the first prosthetic end plate 20 and the second prosthetic end plate 30 even in the case of strong loading.

As can be particularly seen in FIG. 9, the inward facing surface 25 of the prosthetic end plate 20 beginning from the outer edge 23 of the hemispherical shaped recess 21 and the inward facing surface 35 of the second prosthetic end plate 30 beginning from the outer edge 34 of the essentially planar recess 31 extend at an inclination α31 or as the case may be α32 decreasing outwardly. Thereby it is ensured, that in the extreme situation, in which the first prosthetic end plate 20 lies against the second prosthetic end plate 30 (see for example FIGS. 5a, 5b, 7a and 7b), the contact between the first prosthetic end plate 20 and the second prosthetic end plate 30 does not produce a single contact point, but rather occurs along a radially running line. The load is thus distributed over this contact line, whereby the loading of high pressures to a single point is avoided and therewith damaging of the inward facing surfaces 25, 35 of the prosthetic end plates 20, 30 can be avoided.

The inclination α31 and α32 of the inward facing surfaces 25, 35 of the first and second prosthetic end plates 20, 30 lie between 5 and 15°, depending on how great of a tilt angle between the prosthetic end plates 20, 30 is to be made possible.

As materials for the prosthetic core 10 and the two prosthetic end plates 20, 30, biocompatible materials are employed, since the prosthesis is to be employed in the human body. For the prosthetic end plates 20, 30 it is preferred to use metallic materials, for example titanium, titanium alloys or surgical or implant steel. For the prosthetic core 10 preferably suitable synthetic or plastic materials are employed, since a synthetic or plastic is less hard than the metal and better simulates the cushioning effect of a vertebral disk.

REFERENCE NUMBER LIST 10 prosthetic core
11 hemispherical segment
12 planar surface
13 curved surface
15 flat segment
16 outer surface
17 base surface (of the flat segment)
18 groove
20 first prosthetic end plate
21 hemispherical shaped recess
23 outer edge
25 inward facing surface
26 outward facing surface
29 tooth
30 second prosthetic end plate
31 planar recess
32 base surface (of the planar recess)
33 outer wall
34 outer edge
35 inward facing surface
36 outward facing surface
39 tooth
100 vertebra
101 pivot point
R1 radius (of the planar recess)
R2 radius (of the flat segment)
R3 radius (of the hemispherical shaped recess)
R4 radius (of the hemispherical segment)
h main axis
n minor axis
a rotation axis
d1 diameter (of the planar recess)
d1' diameter (of the planar recess at the outer edge)
d2 diameter (of the flat segment)
d3 diameter (of the prosthetic core)
α1 angle
α2 angle
α31 tilt
α32 tilt
B height

The invention claimed is:

1. An intervertebral prosthesis, comprising:
a first prosthetic end plate (20) and a second prosthetic end plate (30), as well as a prosthetic core (10) located between the first prosthetic end plate (20) and the second prosthetic end plate (30),
wherein the first prosthetic end plate (20) has a hemispherical shaped recess (21) with a radius (R3), in which a hemispherical segment (11) of the prosthetic core (10) is seated,
wherein the second prosthetic end plate (30) has an essentially planar recess (31), in which an essentially flat segment (15) of the prosthetic core (10) sits, which transitions to the hemispherical segment (11), the essentially planar recess (31) narrowing conically inward to form an essentially planar recess overhang;

wherein the essentially planar recess (31), having an outer wall (33), exhibits an essentially round cross-section with a diameter (d1), wherein the essentially flat segment (15) exhibits an essentially round cross-section with a diameter (d2), wherein the diameter (d2) of the essentially flat segment (15) is smaller than the diameter (d1) of the essentially planar recess (31), a circumferential groove (18) located on the prosthetic core (10) where the essentially flat segment (15) transitions to the hemispherical segment (11) such that the hemispherical segment (11) forms a hemispherical segment overhang;

wherein the essentially flat segment (15) has an outer surface (16) that corresponds to the outer wall (33) and narrows conically inward, narrowing from the seating of the essentially flat segment (15) in the essentially planar recess (31) towards the hemispherical segment (11); and wherein the essentially planar recess overhang inserts in the groove (18) and the hemispherical segment overhang projects over the essentially planar recess overhang to prevent dislodgment of the prosthetic core (10) when the prosthetic core (10) is slid to one side of the essentially planar recess (31).

2. The intervertebral prosthesis according to claim 1, wherein the diameter (d2) of the essentially flat segment (15) is approximately 14 mm to 22 mm.

3. The intervertebral prosthesis according to claim 1, wherein the diameter (d1) of the essentially planar recess (31) is 19 mm to 27 mm.

4. The intervertebral prosthesis according to claim 1, wherein the base surface (32) of the essentially planar recess (31) exhibits a camber or curvature with a radius (R1).

5. The intervertebral prosthesis according to claim 4, wherein the radius (R1) of the base surface (32) of the essentially planar recess (31) is five to ten times as great as the radius (R3) of the hemispherical recess.

6. The intervertebral prosthesis according to claim 4, wherein the radius (R1) of the base surface (32) of the essential planar recess (31) is approximately 80 mm to 120 mm.

7. The intervertebral prosthesis according to claim 1, wherein the radius (R3) of the hemispherical shaped recess (21) is approximately 8 mm to 14 mm.

8. The intervertebral prosthesis according to claim 7, wherein the radius (R2) of the curvature of the base surface (17) of the essentially flat segment (15) corresponds to the radius (R1) of the curvature of the base surface (32) of the essential planar recess (31).

9. The intervertebral prosthesis according to claim 1, wherein the base surface (17) of the essentially flat segment (15) exhibits a curvature with a radius (R2).

10. The intervertebral prosthesis according to claim 1, wherein an angle $\alpha 1$ of the outer surface (16) of the flat segment (15) relative to the base surface (17) of the flat segment (15) is smaller than 90°.

11. The intervertebral prosthesis according to claim 10, wherein an angle $\alpha 2$ between the outer wall (33) of the essentially planar recess (31) and the base surface (32) of the essentially planar recess (31) is less than 90°.

12. The intervertebral prosthesis according to claim 11, wherein an angle $\alpha 1$ corresponds to an angle $\alpha 2$.

13. The intervertebral prosthesis according to claim 1, wherein the inward facing surface (25) of the first prosthetic end plate (20) is sloped at an angle $\alpha 31$ falling outward, beginning from the outer edge (22) of the hemispherical recess, and the inward facing surface (35) is sloped at an angle $\alpha 32$ falling outwards from the outer edge (34) of the essentially planar recess (31).

14. The intervertebral prosthesis according to claim 13, wherein the angles $\alpha 31$, $\alpha 32$ range from 5 to 15°.

15. An intervertebral prosthesis, comprising:

a first prosthetic end plate (20) having a hemispherical shaped recess (21) with a radius (R3);

a second prosthetic end plate (30) having an essentially planar recess (31), having an outer wall (33) and exhibiting an essentially round cross-section with a diameter (d1), the essentially planar recess (31) narrowing conically inward to form an essentially planar recess overhang;

a prosthetic core (10) having a hemispherical segment (11) seated in the hemispherical shaped recess (21) and an essentially flat segment (15) that is slidably seated in the essentially planar recess (31) and that transitions to the hemispherical segment (11) and exhibits an essentially round cross-section with a diameter (d2);

wherein the diameter (d2) of the essentially flat segment (15) is smaller than the diameter (d1) of the essentially planar recess (31);

a circumferential groove (18) located on the prosthetic core (10) where the essentially flat segment (15) transitions to the hemispherical segment (11) such that the hemispherical segment (11) forms a hemispherical segment overhang;

wherein the essentially flat segment (15) has an outer surface (16) that corresponds to the outer wall (33) and narrows conically inward, narrowing from the seating of the essentially flat segment (15) in the essentially planar recess (31) towards the hemispherical segment (11); and wherein the essentially planar recess overhang inserts in the groove (18) and the hemispherical segment overhang projects over the essentially planar recess overhang to prevent dislodgment of the prosthetic core (10) when the prosthetic core (10) is slid to one side of the essentially planar recess (31).

* * * * *